(12) United States Patent
Smith et al.

(10) Patent No.: US 8,019,401 B1
(45) Date of Patent: Sep. 13, 2011

(54) STRETCHABLE ELECTRODE AND METHOD OF MAKING PHYSIOLOGIC MEASUREMENTS

(75) Inventors: Michael Smith, Oradell, NJ (US); Lloyd Marks, Westfield, NJ (US)

(73) Assignee: Smithmarks, Inc., Ridgefield, NJ (US)

( * ) Notice: Subject to any disclaimer, the term of this patent is extended or adjusted under 35 U.S.C. 154(b) by 1273 days.

(21) Appl. No.: 11/633,077

(22) Filed: Dec. 4, 2006

(51) Int. Cl.
*A61B 5/04* (2006.01)
*A61B 5/053* (2006.01)

(52) U.S. Cl. ........ 600/382; 600/384; 600/386; 600/506; 600/547

(58) Field of Classification Search .............. 600/382, 600/384, 386, 506, 547
See application file for complete search history.

(56) References Cited

U.S. PATENT DOCUMENTS

| | | | |
|---|---|---|---|
| 3,340,867 A | | 9/1967 | Kubicek et al. |
| 3,542,010 A * | | 11/1970 | Love .......................... 600/384 |
| 3,560,845 A * | | 2/1971 | Goldberg et al. ............. 324/243 |
| 3,871,359 A * | | 3/1975 | Pacela .......................... 600/547 |
| 4,016,868 A * | | 4/1977 | Allison ......................... 600/388 |
| 4,308,872 A | | 1/1982 | Watson et al. |
| 4,452,252 A | | 6/1984 | Sackner |
| 4,548,211 A * | | 10/1985 | Marks .......................... 600/507 |
| 5,031,621 A * | | 7/1991 | Grandjean et al. ............. 600/377 |
| 5,040,540 A * | | 8/1991 | Sackner ........................ 600/485 |
| 5,143,089 A * | | 9/1992 | Alt ................................. 607/121 |
| 7,147,601 B2 * | | 12/2006 | Marks et al. .................. 600/500 |
| 7,319,895 B2 * | | 1/2008 | Klefstad-Sillonville et al. ........................ 600/388 |
| 7,499,742 B2 * | | 3/2009 | Bolea et al. ................... 600/372 |

* cited by examiner

*Primary Examiner* — Lee Cohen
(74) *Attorney, Agent, or Firm* — Blank Rome LLP

(57) ABSTRACT

A stretchable electrode for use in physiologic measurements on a human body, such as peripheral impedance plethysmography, is disclosed. One embodiment of the stretchable electrode comprises an uninsulated stainless steel wire braid formed into a tubular conductor surrounding an elastic core and attached to an elastic substrate or base. Other embodiments of the stretchable electrode include a garter spring, a flat braided or woven conductor and an undulating wire. The electrode is placed about a limb of a human body and elastically stretched so that the conductor is in substantially continuous circumferential electrical contact with the skin of the limb. A method of attaching the stretchable electrode to the limb of a human body is also disclosed.

17 Claims, 6 Drawing Sheets

STRETCHABLE ELECTRODE AND METHOD OF MAKING PHYSIOLOGIC MEASUREMENTS

REFERENCE TO RELATED APPLICATIONS

The following commonly assigned patent applications disclose and claim subject matter related to the subject matter of the present invention: U.S. patent application Ser. No. 10/392,308, filed Mar. 20, 2003, entitled "Peripheral Impedance Plethysmography Electrode and System with Detection of Electrode Spacing;" U.S. patent application Ser. No. 10/673,167, filed Sep. 30, 2003, entitled "Methods of Diagnosis Using Pulse Volume Measurement;" U.S. patent application Ser. No. 10/673,328, filed Sep. 30, 2003, entitled "Signal Averaging Using Gating Signal Obtained from Autocorrelation of Gating Signals;" and U.S. patent application Ser. No. 10/759,130, filed Jan. 20, 2004, entitled "Method and Device for Measuring Peripheral Vascular Function." The disclosures of those applications are hereby incorporated by reference in their entireties into the present application.

BACKGROUND OF THE INVENTION

1. Field of the Invention

The present invention relates to electrodes for use in physiologic measurements, including measurements for medical diagnostic procedures, and more particularly to an electrode that is stretchable or elastic in at least one direction to provide reliable low impedance electrical contact with the skin. As used herein in connection with the invention, the terms "elastic," "stretchable" and "elastically stretched" refer to the property of a material or element in which a restoring force is created along an axis of the material or element when a compressive force, or a tensile force less than the elastic limit of the material or element, is applied to it along that axis.

The stretchable electrode of the present invention is especially adapted for use in forming reliable, substantially continuous electrical contact with an annular or circumferential region of the skin about a limb, extremity or other portion (neck, chest, penis, etc.) of a human body, e.g., when making peripheral blood flow measurements as described in the aforementioned related applications. The invention also relates to physiologic measuring methods and in particular to a method of using a stretchable electrode for forming reliable, substantially continuous electrical contact with an annular or circumferential region of the skin about a limb or extremity of a human body, for example, in medical diagnostic procedures, such as peripheral impedance plethysmography.

2. Description of the Prior Art

The need for making reliable electrical contact with the skin of the human body during physiologic measurements, including medical diagnostic procedures is self-evident. Direct contact of conventional metal electrodes with the skin generally provides an unreliable electrical contact, especially circumferential electrical contact with the skin about a limb of the body. Heretofore, electrical contact with the skin has typically been accomplished using disposable electrodes that are coated with or embedded in a conductive paste or adhesive layer. Adhesive-coated electrodes are sometimes uncomfortable for the patient, especially when they are removed from the skin. Paste-coated electrodes often do not make the necessary low impedance electrical contact with the skin that is needed for some physiologic measurements and require cleanup after use.

For certain diagnostic procedures, such as monitoring heart rate while exercising on a treadmill, i.e., a "stress test," the use of disposable, adhesive- or paste-coated electrodes is sometimes neither practical nor economically feasible. In such circumstances, it would be desirable to have a reusable electrode that makes reliable low impedance electrical contact with the skin without the need for a conductive adhesive or paste. In still other diagnostic procedures, adhesive- or paste-coated, disposable electrodes often do not provide sufficient electrical contact with the skin that is necessary for achieving accurate results.

To make high quality impedance plethysmographic measurements of a body segment, a circumferential quadripolar electrode system can be employed which uses two outer current source electrodes paired with two inner voltage measurement electrodes. A typical quadripolar electrode system is shown in FIG. 1 labeled "Prior Art." A constant alternating current is applied to the outer electrodes A, B. The voltage is then measured between the inner electrodes C, D. The impedance of the limb segment L between the inner electrodes can then be calculated.

The current distribution through the limb segment L must be as uniform as possible. If there are gaps in the contact of the circumferential current source electrode with the skin, there will be portions of the limb segment through which there is little or no current and the volume of the limb segment will be underestimated. This will result in inaccurate measurements. To make reliable, continuous, circumferential contact with the limb segment, adhesive electrodes using a conductive hydrogel have been conventionally used. Such electrodes must be disposable for hygienic reasons. However, there are applications in which reusable electrodes are preferred, in particular, when frequent spot measurements are made, such as for vascular screening in a physician's office. Disposing of multiple quadripolar electrodes for these tests would be prohibitively expensive.

With respect to a quadripolar electrode system, from a practical standpoint, it is not desirable for the user to have to place four separate electrodes on each limb to create the quadripolar arrangement but, rather, to place each current-voltage pair together in a single array. Because the limbs of the body are not truly cylindrical, but are shaped more in the form of truncated cones, the circumferential lengths of the electrodes must differ to account for the different circumferences of the limb along its length.

U.S. Pat. No. 3,340,867 to Kubicek et al. discloses an impedance plethysmograph which employs four band electrodes positioned to encircle the neck and thorax. The electrodes comprise a pair of excitation electrodes formed from tinned braided copper wires and a pair of measuring electrodes also formed from tinned braided copper wires. According to the patentees, the braid is stretched to a width of about one centimeter and coated on its inner side with an electrode paste to provide low impedance skin contact. Because the braided electrode is stretched out before it is applied to the skin of the neck and thorax, it has no restoring force that aids in maintaining reliable low impedance contact with the skin, i.e., it is not elastic. Consequently, an electrode paste is required to provide the necessary low impedance skin contact.

U.S. Pat. No. 4,452,252 to Sackner discloses an apparatus and method for monitoring cardiac parameters using an extensible conductor adapted to be looped about the neck or other body portion. Changes in the inductance of the loop provide cardiac and pulmonary information. The conductive loop is made extensible by forming an insulated conductor into undulating, loops supported on an elastic tube. The conductive loop does not, however, make electrical contact with the skin of the subject, but is insulated from the skin.

U.S. Pat. No. 4,308,872 to Watson et al. discloses a method and apparatus similar to that of U.S. Pat. No. 4,452,252 to Sackner for monitoring respiration volumes. The apparatus of Watson et al. also uses an extensible conductor attached to the fabric of a tubular stretch bandage disposed on the body of a patient and measures the inductance of the conductor as the patient breathes. The extensible conductor is formed of insulated wire and, like that of Sackner, does not make conductive electrical contact with the skin.

The foregoing and other prior art electrodes used in physiologic measurements have not provided a reusable electrode that is characterized by a reliable low impedance electrical contact with the skin. It would be desirable, therefore, to provide a reusable electrode especially useful for physiologic measurements that can be easily applied directly to the skin without conductive adhesives or pastes and that makes substantially continuous, low impedance electrical contact with the skin of a subject or patient.

It would also be desirable to provide such an electrode that is readily sterilizable by conventional sterilization techniques, e.g., wiping or spraying with sterile alcohol.

SUMMARY OF THE INVENTION

The present invention provides an electrode that is used in conjunction with apparatus for making physiologic measurements on a human body for various purposes, including medical diagnostic procedures, and especially for making impedance plethysmographic measurements. The invention also relates to a method of using the electrode for forming reliable, substantially continuous electrical contact with an annular or circumferential region of the skin about a limb or extremity of a human body, for example, in medical diagnostic procedures, such as peripheral impedance plethysmography.

According to its apparatus aspects, a first embodiment of the electrode invention comprises a conductive tubular element having an elastic or stretchable core. The conductive element is preferably made from uninsulated stainless steel wires braided or otherwise woven in the form of a tube that can be elongated or compressed along its longitudinal axis. Stainless steel braided jackets for hoses are well known in the fluid flow art, especially in the plumbing and automotive arts. The tubular stainless steel braid is provided with an elastic or stretchable core preferably made of a synthetic rubber cord or tube, such as Neoprene or any other suitable rubber. The elastic core is affixed to the tubular braid so that, when the tubular braid is elongated or stretched along its longitudinal axis, the core provides a restoring force along such axis that returns the tubular braid to its original, unstretched length. Similarly, when the tubular braid is compressed along its longitudinal axis, the core also provides a restoring force along such axis that returns the tubular braid to its original, uncompressed length. The combination of the stainless steel tubular braid and its elastic core render the conductive electrode of the first embodiment elastic or stretchable.

The tubular conductive electrode of the invention preferably has a circular cross-section. However, it is not essential that the cross-section be circular and the electrode may be woven or otherwise constructed with other cross-sectional shapes. For example, the electrode may have an oval, square, rectangular, or rounded rectangular cross-section so long as the electrode is elastically stretchable along its longitudinal axis.

The stretchable conductive electrode of the first embodiment may be used for making physiologic measurements by, for example, wrapping four electrodes circumferentially about a limb of a patient to form a quadripolar electrode system useful in making impedance plethysmograph measurements as described above. Preferably, the electrodes are secured about the limb by any suitable means in a slightly stretched condition to assure that the metal of the conductor is in substantially continuous circumferential contact with the limb and, therefore, make a reliable low impedance electrical contact with the skin of the limb.

The stretchable conductive electrode may be attached, e.g., adhesively or by stitching, to an elastic substrate or base that is preferably made of synthetic rubber sheet material, such as Neoprene or any other suitable rubber. The manner of attachment of the stretchable conductive electrode to the base must allow the components to stretch together and the elastic base may also provide additional restoring force for the conductive electrode when it is stretched or compressed.

If necessary or desired, the electrodes may be slightly moistened with water to improve the electrical contact between the uninsulated metal wires and the skin, i.e., lower the impedance. Alternatively, the elastic base is moisture impervious or can be made from a moisture impervious material so that when the stretchable conductive electrode is wrapped, for example, about a limb, the elastic base covers the electrode and an annular portion of the skin adjacent the circumferential electrode contact area. Because the annular skin portion is covered by the moisture impervious base, it will tend to perspire more than it would if left uncovered. Such perspiration will, in most cases, provide sufficient moisture to improve the conductivity between the electrode and the skin, i.e., lower the impedance between the electrode and the skin.

Although stainless steel is the preferred metal wire for the conductor because of its property of non-corrosiveness, conductive metal wires other than stainless steel wires, e.g., copper wires, aluminum wires, etc., may be used for the electrode of the invention.

According to a second embodiment of the invention, the electrode can be constructed in the form of a garter spring made from uninsulated stainless steel wire with a very small pitch, preferably a pitch no greater than the diameter of the wire, i.e., with adjacent coils touching. The pitch should necessarily be small so as to avoid pinching the skin between the coils of wire. In the case of the second embodiment, the spring itself is inherently elastic so that it is not necessary to provide an axial restoring force such as the elastic core of the first embodiment.

The stretchable conductive electrode of the second embodiment may be attached to an elastic, moisture impervious substrate or base which may function in the same manner as the moisture impervious substrate or base of the first embodiment.

According to a third embodiment of the invention, the electrode is constructed as an uninsulated braided or woven metal wire conductor in the form of a substantially flat band that can be longitudinally elongated. In one construction, the conductor may be a tubular wire braid that has been flattened to form a substantially flat band. Preferably, the conductor is made from non-corrosive wires, such as stainless steel wires.

In its neutral state, i.e., neither elongated nor compressed along its longitudinal axis, the flat conductor is attached to an elastic substrate or base, such as a strip of synthetic rubber, to provide the necessary restoring force to make the conductor elastically stretchable. The elastic substrate of the third embodiment may also be moisture impervious so as to function in the same manner as the moisture impervious substrate or base of the first and second embodiments.

The conductor can be attached to the elastic substrate by any suitable means, such as adhesively or by stitching. While the conductor may be in direct physical contact with the skin, it is preferably sandwiched between two elastic, electrically conductive adhesive hydrogel layers or otherwise embedded in an elastic, electrically conductive adhesive hydrogel sheet. In this third embodiment, because the hydrogel layers adhere to the skin of the subject as well as to the substrate, the electrode would be intended for single use and would, therefore, be disposable.

According to a fourth embodiment of the invention, the electrode is constructed as a conductor comprising an uninsulated metal wire or wires having an undulating shape, e.g., a sine wave shape, and is elastic or stretchable along the axis of undulation. Preferably, the wire or wires are made from a non-corrosive metal, such as stainless steel. As used herein in connection with the invention, the term "undulating" refers to any shape of the wire that permits the wire to be elastically stretched in a plane containing the wire and the axis about which it undulates (its "undulation axis"). Such shapes include, but are not limited to, a sine wave shape, a zigzag or sawtooth shape, a square wave shape and the like.

As in the third embodiment, in its neutral state, i.e., neither elongated nor compressed along its undulation axis, the undulating conductor is attached to an elastic substrate or base, such as a strip of synthetic rubber. The conductor undulates in a plane parallel to the substrate and is elastically stretchable along its undulation axis and, therefore, inherently provides the necessary restoring force to make the electrode elastically stretchable. The elastic substrate of the fourth embodiment may also be moisture impervious so as to function in the same manner as the moisture impervious substrate or base of the other embodiments.

The undulating conductor is attached to the elastic substrate by any suitable means, such as adhesively or by stitching. While the undulating conductor may be in direct physical contact with the skin, it is preferably sandwiched between two elastic, electrically conductive adhesive hydrogel layers or otherwise embedded in an elastic, electrically conductive adhesive hydrogel sheet. In this fourth embodiment, because the hydrogel layers adhere to the skin of the subject as well as to the substrate, the electrode would be intended for single use and would, therefore, be disposable.

According to the method aspects of the present invention, a stretchable conductive electrode having an axial length and two ends is wrapped about a limb or extremity of a subject with the ends overlapping and the electrode in substantially continuous circumferential electrical contact with the skin of the subject. The electrode is then stretched to generate a restoring force along the axial length of the electrode and the overlapped portions are fastened together so as to maintain the electrode in its elastically stretched condition.

The stretchable electrode of the invention also is advantageously used in a quadripolar electrode system. As previously mentioned, because the limbs of the body are not truly cylindrical, but are shaped more in the form of truncated cones, the circumferential lengths of the electrodes in a quadripolar electrode system must differ to account for the different circumferences of the limb along its length. Because the electrodes of the invention are elastic or stretchable, when arranged in a quadripolar electrode array, they are able to stretch independently of one another so as to make reliable, substantially continuous and uniform, circumferential electrical contact with the skin of the limb at each axial position along the limb.

With the foregoing and other objects, advantages and features of the invention that may become hereinafter apparent, the nature of the invention may be more clearly understood by reference to the following detailed description of the invention, the appended claims and to the several drawings forming a part hereof.

DETAILED DESCRIPTION OF THE INVENTION

Figure 1:
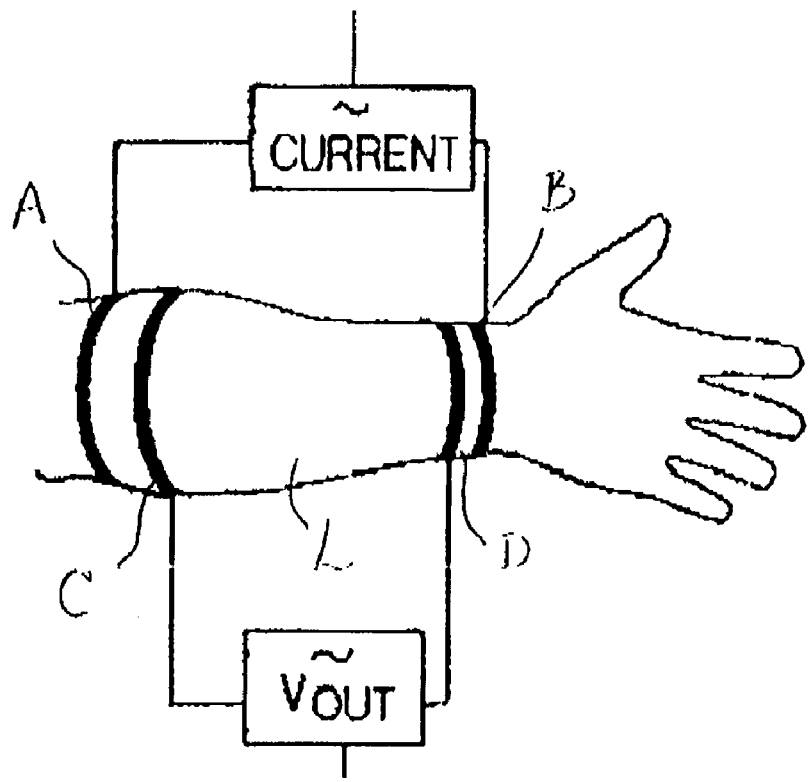
FIG. 1 is a schematic view of a conventional circumferential quadripolar electrode system useful for making peripheral impedance plethysmographic measurements of the human body.
Figure 2:
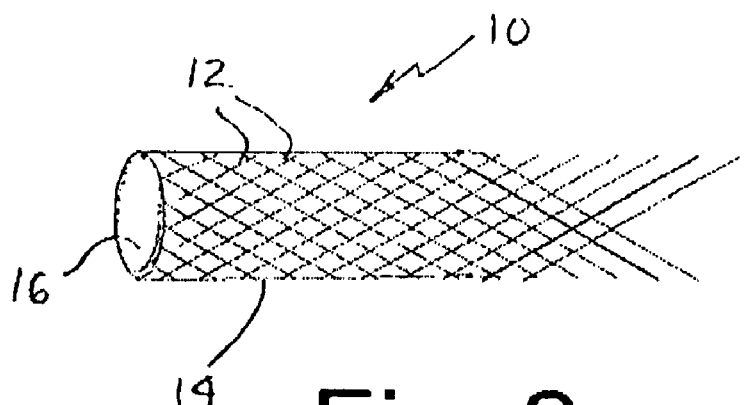
FIG. 2 is a partial perspective schematic view of the first embodiment of the electrode of the invention shown in a stretched condition.
Figure 3:
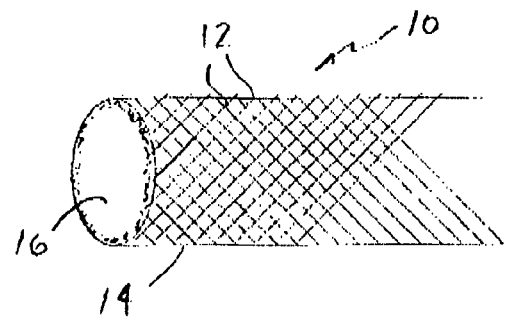
FIG. 3 is a partial perspective schematic view of the first embodiment of the electrode of the invention shown in a compressed condition.

Referring now to FIGS. 2-7 of the drawings, a first embodiment of the stretchable electrode of the invention is illustrated. FIGS. 2 and 3 are schematic views of a conductive element or electrode 10 that is formed from uninsulated conductive metal wires 12, such as stainless steel wires, into a tubular braid 14 of a type well known in the electronic, automotive and plumbing arts. The braid 14 can be elongated as shown in FIG. 2 or compressed as shown in FIG. 3, but is not inherently axially elastic, that is, by itself it has little or no restoring force to return it to its original unstretched or uncompressed length. For that purpose, according to the invention, an elastic central core 16 is provided coaxially inside the braid 14 in a tight-fitting relation with the braid 14. The elastic core may be a rod or tube of a synthetic rubber, such as Neoprene or other suitable rubber. When the braid 14 with its elastic core 16 is stretched as shown in FIG. 2, the core generates an elastic restoring force that returns the braid 14 to its original, unstretched condition. Similarly, when the braid 14 with its elastic core 16 is compressed as shown in FIG. 3, the core generates an elastic restoring force that returns the braid 14 to its original, uncompressed condition.

The wires 12 of the conductive electrode 10 may be made of any conductive metal, e.g., aluminum, copper, etc., but stainless steel is preferred because of its non-corrosiveness and minimal oxidation. The cross-section of the braid 14 is shown as circular, however, the braid 14 may be formed with other cross-sections, such as oval, square, rectangular, rounded rectangular.

The conductive electrode 10 may be used in the form shown in FIGS. 2 and 3 to make electrical contact with the skin of a subject, for example, by wrapping a given length of the electrode about the limb of a subject with the ends of the electrode overlapping and securing the overlapping ends together so that the electrode 10 is in its stretched condition, thereby insuring that the uninsulated metal wires 12 of the braid 14 are in substantially continuous circumferential electrical contact with the skin of the limb. A low voltage alternating current may be applied to the electrode as described in the above-referenced related applications. If two or more electrodes 10 are used they can be independently stretched about the limb to accommodate the different circumferential lengths around a limb depending on the axial position of the limb where the electrodes are placed.

Figure 4:
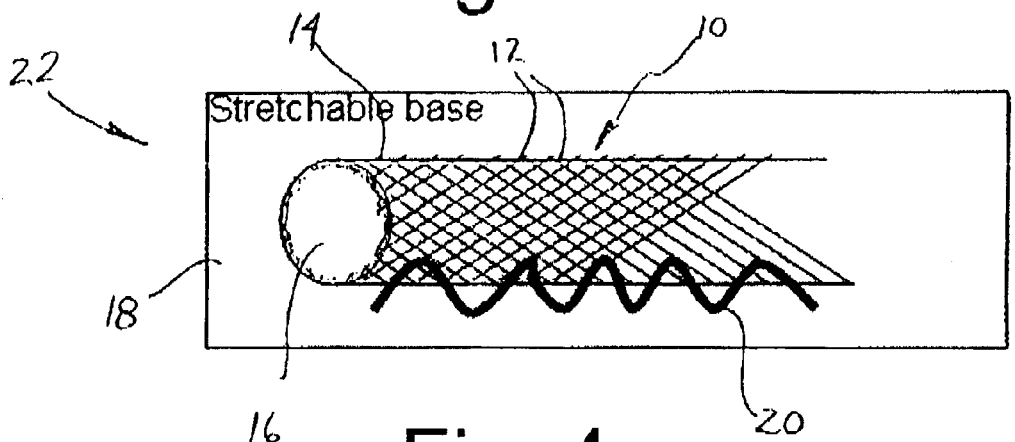
FIG. 4 is a perspective schematic view of the first embodiment of the electrode invention shown attached to a stretchable base.

Referring now to the schematic representation of FIG. 4, the conductive electrode 10 may also be attached to an elastic or stretchable substrate or base 18 by stitching 20 or by any other suitable means, such as an adhesive, to form an electrode assembly 22. In whatever form, the attachment of the electrode 10 to the elastic substrate 18 must allow the components to stretch together. The electrode assembly 22 is used to make electrical contact with the skin of a subject, for example, by wrapping a given length of the electrode assembly 22 about the limb of a subject with the ends of the electrode assembly 22 overlapping and securing the overlapping ends together so that the electrode 10 is in its stretched condition, thereby insuring that the uninsulated metal wires 12 of the braid 14 are in substantially continuous circumferential electrical contact with the skin of the limb.

Figure 5:
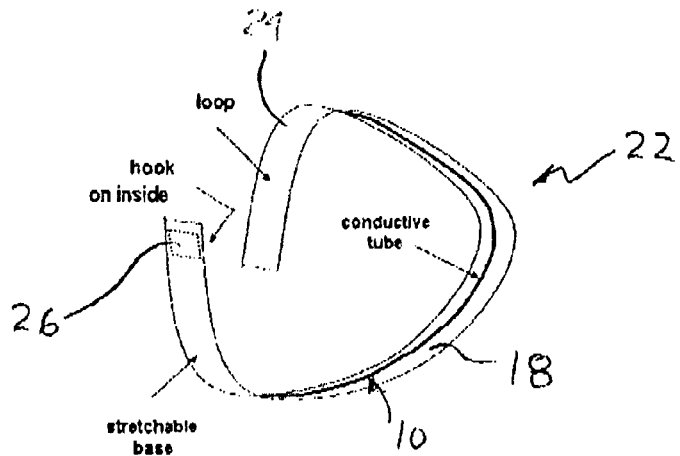
FIG. 5 is a perspective view of the first embodiment of the electrode invention shown with hook-and-loop material fasteners for securing the electrode to an extremity of the body.

FIG. 5 illustrates one construction of the electrode assembly 22 that can be advantageously used. In this construction, the elastic substrate 18 is an elongated, preferably moisture impervious, elastic band that provided on its side opposite the electrode 10 with an elastic loop fabric 24 or with several axially spaced strips of loop fabric 24. On the electrode-side of the substrate 18 a section of hook fabric 26 is attached. To use the electrode assembly 22 of FIG. 5, the assembly 22 is wrapped about the limb of a subject with the electrode in direct contact with the skin of the limb and the ends of the assembly overlapped. The assembly 22 is stretched to insure that the uninsulated metal wires 12 of the braid 14 are in substantially continuous circumferential electrical contact with the skin of the limb and the hook material 26 is secured to the loop material 24 at an appropriate position to maintain the assembly in a stretched condition for making measurements.

Prior to wrapping the electrode assembly 22 about the limb, the electrode 10 may be moistened with water to improve the low impedance electrical contact between the electrode and the skin. Advantageously, any perspiration of the skin caused by securing the moisture impervious substrate band 18 over the skin will also improve the low impedance electrical contact between the electrode and the skin.

Figure 6:
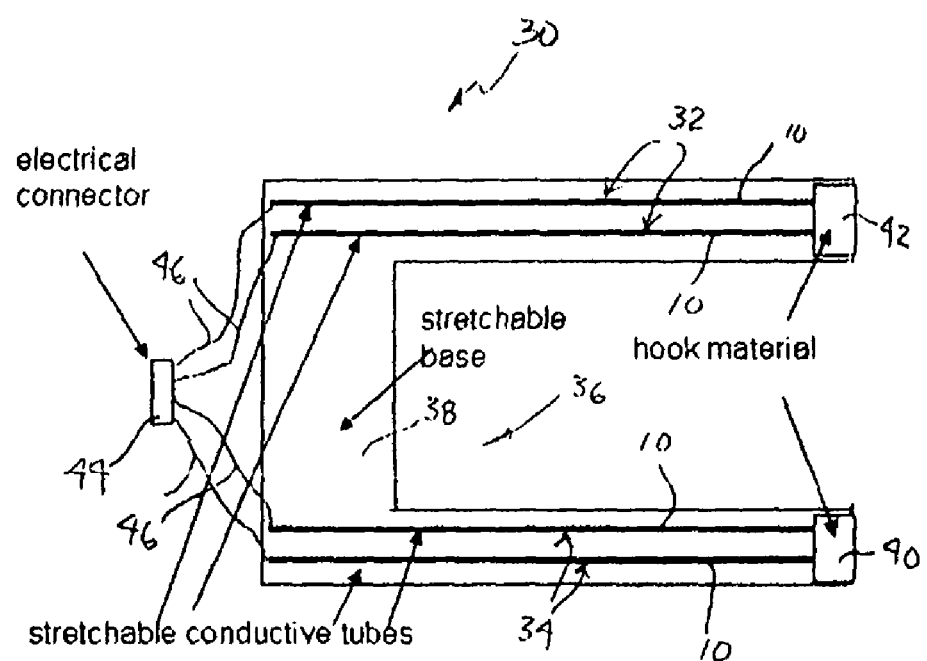
FIG. 6 is a plan view showing the electrode of the invention used in a quadripolar electrode system especially adapted for making peripheral impedance plethysmographic measurements.

FIG. 6 illustrates in plan view the stretchable conductive electrode of the invention formed into a quadripolar electrode array 30 with four stretchable electrodes 10 arranged in two parallel pairs on arms 32, 34 of an elastic or stretchable base 36. The electrode pairs on arms 32, 34 are spaced apart a predetermined distance by a transverse bridge section 38 of the base 36. The back side of the base 36 (as viewed in FIG. 6) is provided with a stretchable loop fabric (not shown) and the end of each arm 32, 34 is provided with a rectangular section of hook material 40, 42. An electrical connector 44 is electrically connected to each of the four electrodes 10 by wires 46.

Figure 7:
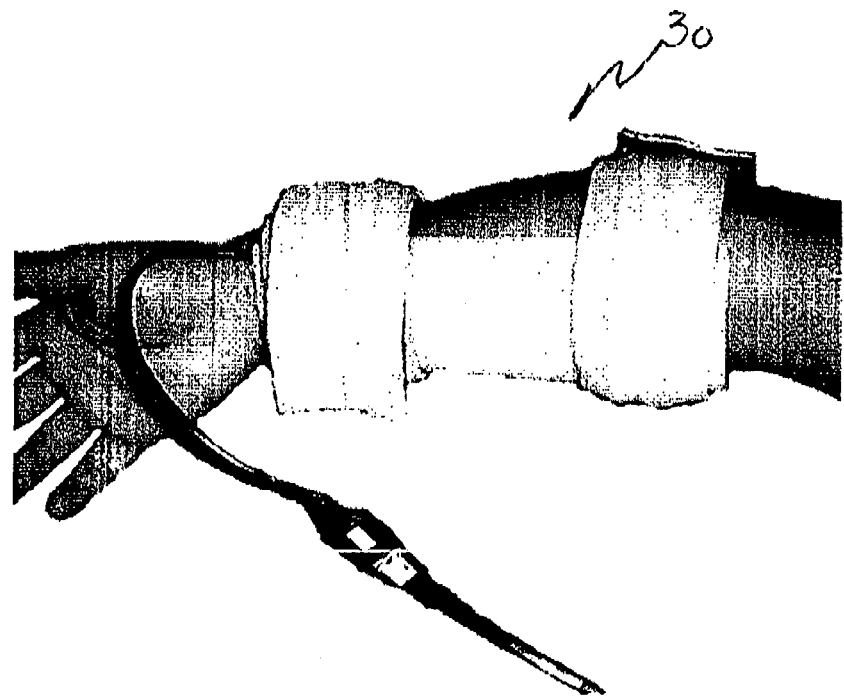
FIG. 7 is a perspective view of the quadripolar electrode system of FIG. 6 shown attached to the limb of a subject for making peripheral impedance plethysmographic measurements.

The particular electrode array construction of FIG. 6 is useful in making peripheral impedance plethysmograph measurements on the human body. FIG. 7 illustrates the quadripolar electrode array 30 of FIG. 6 wrapped about the arm of a subject for making peripheral impedance plethysmograph measurements.

Figure 8:
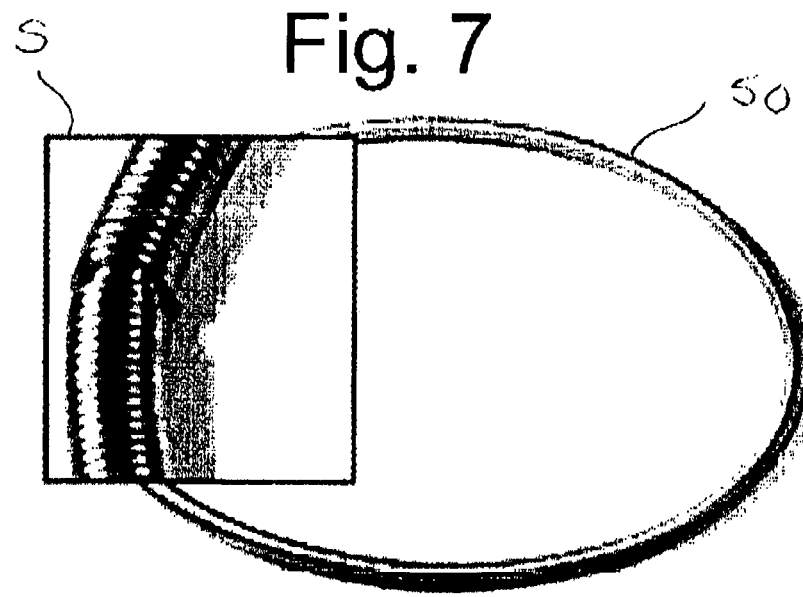
FIG. 8 is a perspective view of the second embodiment of the electrode of the invention.

Referring now to FIG. 8, the second embodiment of the stretchable electrode of the invention is shown in perspective with an enlarged section S. In this embodiment, the stretchable electrode 50 is in the form of a garter spring with a pitch equal to the diameter of the wire used to make the spring, i.e., with adjacent wire coils touching. The garter spring of the stretchable electrode 50 is inherently elastic so that no elastic core is needed. Preferably, an elastic base (not shown) is attached to the outer circumference of the stretchable electrode 50 similar to that of the first embodiment.

Figure 9:
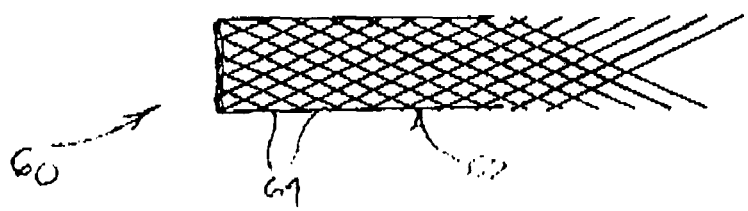
FIG. 9 is a partial perspective schematic view of the third embodiment of the electrode of the invention shown in a stretched condition.
Figure 10:
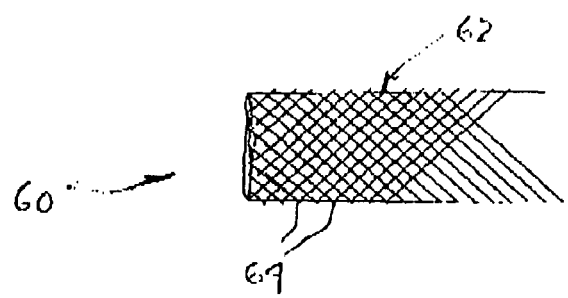
FIG. 10 is a partial perspective schematic view of the third embodiment of the electrode of the invention shown in a compressed condition.
Figure 11:
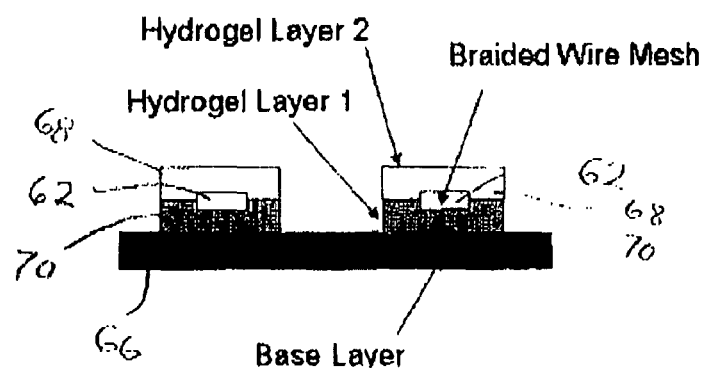
FIG. 11 is a schematic end view of the third embodiment of the electrode invention shown as a pair of electrodes attached to a stretchable base with conductive adhesive hydrogel layers.

The third embodiment of the electrode of the invention is shown in FIGS. 9-11. In this embodiment, the electrode 60 is constructed as an uninsulated braided or woven metal wire conductor in the form of a substantially flat band 62 that can be longitudinally elongated. The band 62 comprises an uninsulated tubular wire braid that has been flattened to form the band. Preferably, the braid is made from non-corrosive wires 64, such as stainless steel wires. FIG. 9 illustrates the band 62 in its elongated state and FIG. 10 illustrates the band 62 in its compressed state. To operate according to the invention, the band 62 must be attached to an elastic substrate.

In its neutral state, i.e., neither elongated nor compressed along its longitudinal axis, the band 62 is attached to an elastic substrate or base 66 (FIG. 11), such as a strip of synthetic rubber, to provide the necessary restoring force to make the conductor elastically stretchable. The elastic substrate 66 of the third embodiment may also be moisture impervious so as to function in the same manner as the moisture impervious substrate or base of the first embodiment.

The band 62 can be attached to the elastic substrate 66 by any suitable means, such as adhesively or by stitching. FIG. 11 illustrates a pair of electrodes formed as bands 62 attached to substrate 66. While the bands 62 may be in direct physical contact with the skin, they are preferably sandwiched between two elastic, electrically conductive adhesive hydrogel layers 68, 70 or otherwise embedded in an elastic, electrically conductive adhesive hydrogel sheet. The hydrogel layers 68 adhere to the skin of the subject and the hydrogel layers 70 adhere to the substrate 66. The electrically conductive, adhesive hydrogel layers 68, 70 are well known in the medical device arts and are used, among other applications, for EKG electrodes.

Figure 12:
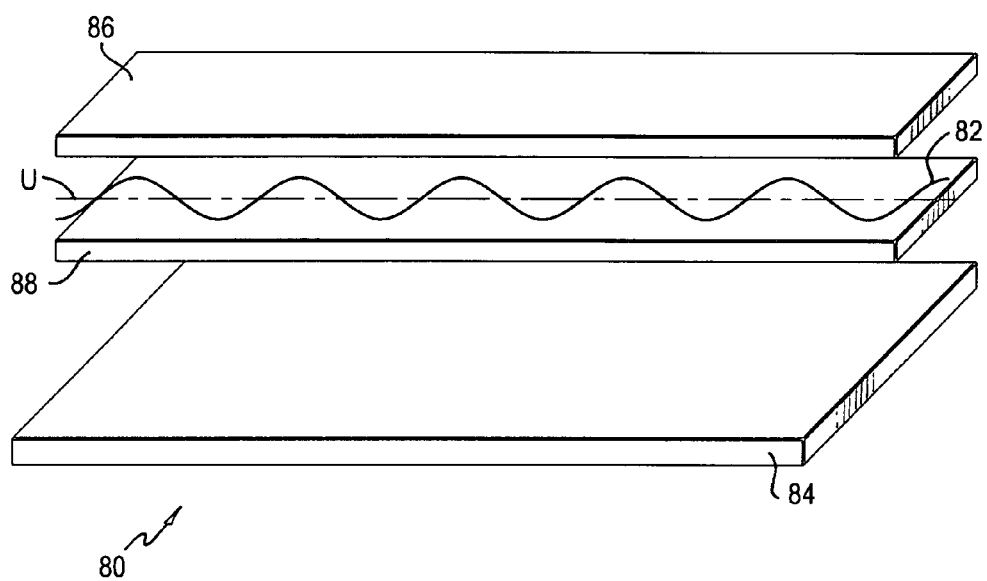
FIG. 12 is an exploded perspective schematic view of the fourth embodiment of the electrode of the invention showing an uninsulated metal wire conductor with an undulating shape.

The fourth embodiment of the invention is schematically illustrated in FIG. 12. In this embodiment, the electrode 80 is constructed as a conductor comprising an uninsulated metal wire or wires 82 having an undulating shape, e.g., a sine wave shape, and is elastic or stretchable along its axis of undulation U. Preferably, the wire or wires 82 are made from a non-corrosive metal, such as stainless steel and may have any shape that permits the wire to be elastically stretched in a plane containing the wire and the axis U about which it undulates.

In its neutral state, i.e., neither elongated nor compressed along its undulation axis U, the undulating wire 82 is attached to an elastic substrate or base 84, such as a strip of synthetic rubber. The elastic substrate 82 may also be moisture impervious so as to function in the same manner as the moisture impervious substrate or base of the other embodiments.

The undulating wire 82 is attached to the elastic substrate by any suitable means, such as adhesively or by stitching. While the wire 82 may be in direct physical contact with the skin, it is preferably sandwiched between two elastic, electrically conductive adhesive hydrogel layers 86, 88 or otherwise embedded in a single elastic, electrically conductive adhesive hydrogel sheet. The hydrogel layer 86 adheres to the skin of the subject and the hydrogel layer 88 adheres to the substrate 84.

It will be apparent that the electrode 80 can be used in a quadripolar array of electrodes for making peripheral impedance plethysmograph measurements, as well as in other electrode arrangements for making various types of physiologic measurements.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. An electrode for making electrical contact with the skin comprising an uninsulated metal conductor adapted to make electrical contact with the skin, said conductor having a longitudinal axis and being elastically stretchable along said axis, wherein said metal conductor comprises a plurality of metal wires woven into a tube which is disposed about an elastic core.

2. The electrode of claim 1, wherein said metal wires are braided into a tubular form and disposed about the elastic core.

3. The electrode of claim 1, wherein said metal wires are stainless steel and the elastic core is a synthetic rubber cord or tube.

4. The electrode of claim 1, wherein said metal conductor has a circular cross-section.

5. The electrode of claim 1, wherein said metal conductor is attached to an elastic substrate.

6. The electrode of claim 5, wherein said metal conductor is attached to said elastic substrate by an adhesive or by stitching.

7. The electrode of claim 5, wherein said elastic substrate is moisture impervious.

8. The electrode of claim 5, wherein said elastic substrate has opposite sides provided with hook and loop material for fastening the metal conductor about the limb of a human subject in an elastically stretched condition of the conductor and with the conductor in substantially continuous circumferential electrical contact with the skin of the limb.

9. The electrode of claim 1, wherein said electrode is sterilizable and reusable.

10. An electrode for making electrical contact with the skin, including four conductors arranged in parallel in a quadripolar array for making peripheral plethysmograph measurements, each of said conductors being an uninsulated metal conductor adapted to make electrical contact with the skin, each of said conductors having a longitudinal axis and being elastically stretchable along said axis, said conductors being attached to an elastic substrate and means affixed to said substrate for fastening said conductors about a limb of a subject with the conductors in an elastically stretched condition.

11. The electrode of claim 10, wherein the conductors are grouped in pairs.

12. The electrode of claim 11, further comprising a bridge connecting the pairs of the conductors.

13. A stretchable electrode adapted for encircling a body portion of a subject and making substantially continuous circumferential electrical contact with the skin of the body portion, comprising an uninsulated metal conductor having a longitudinal axis, said conductor being elastically stretchable along said axis, wherein said metal conductor comprises a plurality of metal wires woven into a tube which is disposed about an elastic core.

14. The electrode of claim 13, wherein said metal conductor is made of a stainless steel wire braid formed into a tube surrounding an elastic core and means connected to said conductor for fastening said electrode about the body portion with the metal conductor in its elastically stretched condition.

15. An electrode for making physiologic measurements of the human body comprising a plurality of metal wires braided into a tubular conductor having a longitudinal axis, an elastic core disposed inside said tubular conductor along said longitudinal axis, and means for attaching the tubular conductor to a portion of the body in an elastically stretched condition with the conductor in substantially continuous electrical contact with the skin of the body portion.

16. The electrode of claim 15, wherein said metal wires are stainless steel wires, said attaching means comprising a moisture impervious substrate to which the tubular conductor is fastened.

17. The electrode of claim 15, including four of said conductors arranged in parallel on said substrate in a quadripolar array for making peripheral plethysmograph measurements, said attaching means fastening said conductors and substrate about a limb of the body with the conductors in an elastically stretched condition.

* * * * *